United States Patent
Inoue et al.

(10) Patent No.: US 7,402,695 B2
(45) Date of Patent: Jul. 22, 2008

(54) METHOD OF SEPARATELY COLLECTING OPTICALLY ACTIVE AMINO ACID AMIDE AND OPTICALLY ACTIVE AMINO ACID

(75) Inventors: Atsushi Inoue, Niigata (JP); Akinori Tanaka, Niigata (JP); Satoshi Nanba, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/587,006

(22) PCT Filed: Apr. 22, 2005

(86) PCT No.: PCT/JP2005/007704

§ 371 (c)(1),
(2), (4) Date: Oct. 20, 2006

(87) PCT Pub. No.: WO2005/102988

PCT Pub. Date: Nov. 3, 2005

(65) Prior Publication Data

US 2007/0213559 A1    Sep. 13, 2007

(30) Foreign Application Priority Data

Apr. 22, 2004  (JP) .............................. 2004-126644

(51) Int. Cl.
*C07C 227/00* (2006.01)
*C07C 237/00* (2006.01)

(52) U.S. Cl. ....................................... 562/554; 564/198

(58) Field of Classification Search .................. None
See application file for complete search history.

(56) References Cited

U.S. PATENT DOCUMENTS 4,605,477 A * 8/1986 Doya et al. .................. 204/530
2003/0171597 A1   9/2003 Katoh et al.

FOREIGN PATENT DOCUMENTS

| EP | 1300392 A1 | 4/2003 |
| JP | 2001-011034 | 1/2001 |
| JP | 2001-328970 | * 11/2001 |
| JP | 2001-328970 A | 11/2001 |
| JP | 2002-37781 A | 2/2002 |
| JP | 2002-241315 A | 8/2002 |
| JP | 2002-253294 A | 9/2002 |

* cited by examiner

*Primary Examiner*—Paul A Zucker
(74) *Attorney, Agent, or Firm*—Fitch, Even, Tabin & Flannery

(57) ABSTRACT

A method for separately collecting an optically active amino acid amide and an optically active amino acid from an aqueous solution containing same, together with at least one member selected from the group consisting of an acid, a base, and a salt, includes a step of neutralizing an acid or base in the aqueous solution, a desalting step of removing a salt contained in the aqueous solution and/or formed in the neutralization step, and a step of separately collecting the optically active amino acid amide/amino acid separately from the desalted aqueous solution by a process which takes advantage of a difference in solubility between the two components in an organic solvent. The desalting step is preferably performed by electrodialysis, optionally with ammonia added to the aqueous solution. The optically active amino acid amide/amino acid can be separately collected with high efficiency using an organic solvent.

7 Claims, No Drawings

METHOD OF SEPARATELY COLLECTING OPTICALLY ACTIVE AMINO ACID AMIDE AND OPTICALLY ACTIVE AMINO ACID

This Application is the National Phase of International Application No. PCT/JP2005/007704 filed Apr. 22, 2005, which designated the U.S. and was not published under PCT Article 21(2) in English, and this application claims, via the aforesaid International Application, the foreign priority benefit of and claims the priority from Japanese Application No. 2004-126644, filed Apr. 22, 2004, the complete disclosures of which are incorporated herein by reference.

TECHNICAL FIELD

The present invention relates to a method of pretreatment of an aqueous solution, which is performed in separately collecting an optically active amino acid amide and an optically active amino acid using an organic solvent from the aqueous solution which contains the optically active amino acid amide and the optically active amino acid together with at least one member selected from the group consisting of acids, bases, and salts. The optically active amino acid amide or the optically active amino acid is an important substance as an intermediate in the production of various industrial chemicals, agricultural chemicals, and pharmaceuticals.

BACKGROUND ART

As a method for producing an optically active amino acid amide and an optically active amino acid, there has been known, for example, an optical resolution method using an enzyme which enantioselectively hydrolyzes one of the optically active forms of an amino acid amide or using a microorganism containing the enzyme. This method is advantageous in that an optical resolution can be performed under a mild condition without use of expensive optical resolving agents and/or devices.

However, in the above-mentioned method of optical resolution of an amino acid amide using an enzyme that enantioselectively hydrolyzes an amino acid amide or a microorganism containing the enzyme, an unreacted optically active amino acid amide coexists with the optically active amino acid as a reaction product in the reacted solution, and thus it is necessary to separate the optically active amino acid amide and the optically active amino acid after the reaction. As a method of this separation, there is known a method of preferentially precipitating and filtering off an optically active amino acid by concentrating a reacted aqueous solution and then adding thereto an organic solvent or by concentrating the aqueous solution with addition of an organic solvent that forms azeotrope with water so as to replace the water with the organic solvent (refer to Patent Document 1).

However, when either of an acid or a base exists together with an optically active amino acid amide and an optically active amino acid in an enzymatically-reacted solution, it is difficult to separate the optically active amino acid amide and the optically active amino acid, because the optically active amino acid amide and the optically active amino acid form acid salts or base salts to become hardly soluble in the organic solvent. Further, when a salt is contained in the enzymatically-reacted solution, there is a problem that the salt is also precipitated together with an optically active amino acid that is obtained as an insoluble matter in the organic solvent, thereby lowering crystal purity and efficiency of collecting the amino acid separately from the optically active amino acid amide.

Patent Document 1: Japanese Patent Laid-open No. 2001-11034

DISCLOSURE OF THE INVENTION

Problems to be Solved by the Invention

The present invention is aimed at solving the above-described problems and to provide an efficient method for separately collecting an optically active amino acid amide and an optically active amino acid from an aqueous solution containing the optically active amino acid amide and the optically active amino acid together with at least one member selected from the group consisting of acids, bases and salts, using an organic solvent.

Means for Solving the Problems

As a result of intensive researches for solving the above-described problems, the inventors have found that an optically active amino acid amide and an optically active amino acid can be separately collected with high purity and efficiency in the following manner: neutralizing acids and bases in an aqueous solution containing an optically active amino acid amide and an optically active amino acid together with at least one member selected from the group consisting of acids, bases and salts, and then desalting the aqueous solution with optional addition of ammonia by use of an ion-exchange membrane process, an electrodialysis process or the like; substituting the solvent of the desalted aqueous solution with an organic solvent, for example, by distilling the aqueous solution under reduced pressure to remove water and then adding thereto an organic solvent, or by distilling the aqueous solution with a solvent that forms azeotrope with water; and then separating the optically active amino acid precipitated as crystals from the optically active amino acid amide dissolved in an organic solvent by means of filtering or the like. Thus, the present invention has been completed.

In other words, the present invention relates to a separately collecting method of an optically active amino acid amide and an optically active amino acid from an aqueous solution containing the optically active amino acid amide and the optically active amino acid together with at least one member selected from the group consisting of an acid, a base and a salt by use of an organic solvent, characterized in that the aqueous solution is previously subjected to neutralization of the acid or base contained therein and then to desalting, and is defined as shown in (1) to (6) below.

(1) A method for separately collecting an optically active amino acid amide and an optically active amino acid from an aqueous solution containing the optically active amino acid amide and the optically active amino acid together with at least one member selected from the group consisting of an acid, a base and a salt, which comprises:

a neutralization step of neutralizing an acid or a base when the aqueous solution contains the acid or the base, a desalting step of removing the salt contained in the aqueous solution and/or formed in the neutralization step, and a step of collecting the optically active amino acid amide and the optically active amino acid separately from each other from the aqueous solution which has been desalted in the desalting step, by a process which takes advantage of a difference in solubility between the two components in an organic solvent.

(2) The method described in (1) above, wherein the desalting step is performed with ammonia added to the aqueous solution.

(3) The method described in (2) above, wherein ammonia is added in an amount of 0.01 to 100 times by mole the optically active amino acid amide.
(4) The method described in (1) or (2) above, wherein the desalting step is performed by an electrodialysis process.
(5) The method described in any one of (1) to (4) above, wherein the optically active amino acid amide is L-2-amino-n-butyric acid amide.
(6) The method described in any one of (1) to (4) above, wherein the optically active amino acid is D-2-amino-n-butyric acid.

Effects of Invention

An optically active amino acid amide and an optically active amino acid can be separately collected with high efficiency by neutralizing an acid or a base in an aqueous solution that contains the optically active amino acid amide and the optically active amino acid together with at least one member selected from the group consisting of an acid, a base and a salt; then desalting the aqueous solution by an electrodialysis process or the like with ammonia being optionally added; and further inducing the formation of an organic solvent phase containing the optically active amino acid amide and a crystal phase of the optically active amino acid, for example, by evaporation of water from the solution followed by addition of an organic solvent.

BEST MODE FOR CARRYING OUT THE INVENTION

The present invention will be described in further detail below. The aqueous solution containing an optically active amino acid amide and an optically active amino acid together with at least one member selected from the group consisting of an acid, a base and a salt is classified into the following five types: (I) an aqueous solution containing an optically active amino acid amide and an optically active amino acid together with an acid, (II) an aqueous solution containing an optically active amino acid amide and an optically active amino acid together with a base, (III) an aqueous solution containing an optically active amino acid amide and an optically active amino acid together with a salt, (IV) an aqueous solution containing an optically active amino acid amide and an optically active amino acid together with an acid and a salt, and (V) an aqueous solution containing an optically active amino acid amide and an optically active amino acid together with a base and a salt. Needless to say, the terms "acid", "base" and "salt" used herein mean other ones than the optically active amino acid amide and the optically active amino acid, and include, for example, an acid, a base or a salt which is added in the production of the amino acid amide, or used for adjustment of pH in the optical resolution of the amino acid amide.

(I) When the aqueous solution contains an optically active amino acid amide and an optically active amino acid together with an acid, the solution is subjected to neutralization of the acid contained therein with a base, and then subjected to, for example, electrodialysis with addition of ammonia to obtain a desalted solution before separation and collection of the optically active amino acid amide and the optically active amino acid using an organic solvent are performed. The base used for the neutralization includes, but is not limited to, ammonia, sodium hydroxide and sodium carbonate. When ammonia is used as the base, the neutralization step and the desalting step may be performed continuously.

(II) When the aqueous solution contains an optically active amino acid amide and an optically active amino acid together with a base, the solution is subjected to neutralization of the base contained therein with an acid, and then subjected to, for example, electrodialysis with addition of ammonia to obtain a desalted solution before separation and collection of the optically active amino acid amide and the optically active amino acid using an organic solvent are performed. The acid used for the neutralization includes, but is not limited to, hydrochloric acid and sulfuric acid.

(III) When the aqueous solution contains an optically active amino acid amide and an optically active amino acid together with a salt, the solution is subjected to, for example, electrodialysis with addition of ammonia to obtain a desalted solution before separation and collection of the optically active amino acid amide and the optically active amino acid using an organic solvent are performed. In this case, the neutralization step can be omitted.

(IV) When the aqueous solution contains an optically active amino acid amide and an optically active amino acid together with an acid and a salt, the solution is subjected to neutralization of the acid contained therein with a base, and then subjected to, for example, electrodialysis with addition of ammonia to obtain a desalted solution before separation and collection of the optically active amino acid amide and the optically active amino acid using an organic solvent are performed. The base used for the neutralization includes, but is not limited to, ammonia, sodium hydroxide and sodium carbonate. When ammonia is used as the base, the neutralization step and the desalting step may be performed continuously.

(V) When the aqueous solution contains an optically active amino acid amide and an optically active amino acid together with a base and a salt, the solution is subjected to neutralization of the base contained therein with an acid, and then subjected to, for example, electrodialysis with addition of ammonia to perform desalting before separation and collection of the optically active amino acid amide and the optically active amino acid using an organic solvent are performed. The acid used for the neutralization includes, but is not limited to, hydrochloric acid and sulfuric acid.

Meanwhile, when the aqueous solution contains only an optically active amino acid amide and an optically active amino acid, the solution can be subjected directly to separation and collection of the optically active amino acid amide and the optically active amino acid using an organic solvent without the neutralization and desalting.

Although the method of desalting performed in the cases (I) to (V) is not specifically restricted, the salt can be effectively removed, for example, by using an electrodialysis process in which a cation exchange membrane, an anion exchange membrane, and a bipolar membrane are appropriately combined as separation membranes. In this instance, leakage of optically active amino acid amides through cation exchange membranes and the resultant loss of the amides can be prevented by adding ammonia to the aqueous solution in an amount of 0.01 to 100 times by mole, preferably 3 to 10 times by mole the optically active amino acid amide and then subjecting the resulting aqueous solution to electrodialysis to perform desalting.

The optically active amino acid amide and the optically active amino acid used in the present invention include, but are not limited to, natural or non-natural types of optically active amino acids, and optically active amino acid amides corresponding thereto, such as 2-amino-n-butyric acid, 2-amino-n-butyric acid amide, t-leucine, t-leucine amide, valine, and valine amide. The aqueous solution containing the optically active amino acid amide and the optically active amino acid includes, but is not limited to, one obtained by a biological optical resolution reaction of a racemic amino acid amide.

Such an aqueous solution is processed into a highly pure aqueous solution containing an optically active amino acid amide and an optically active amino acid with little impurities, through the above-described neutralization step and desalting step. As a result, this aqueous solution can be used to separate the optically active amino acid amide and the optically active amino acid from each other and collect them in high yield in accordance with a process which takes advantage of a difference in solubility between the two components in an organic solvent. Such a process utilizing an organic solvent includes commonly used solvent extraction processes. A specific example thereof includes a process in which the above-mentioned aqueous solution is concentrated by distillation under reduced pressure, and then an organic solvent is added to the solution to precipitate an optical active amino acid preferentially. The organic solvent to be used in this step is not particularly limited as long as the amino acid is insoluble and the amino acid amide is soluble in the solvent. Examples of the solvent include alcohols such as methanol, ethanol, propanol, 2-propanol, 2-methyl-1-propanol, 4-methyl-1-pentanol, and 2-ethyl-1-hexanol. Further, another example of the solvent extraction process includes a process in which an aqueous solution is distilled while it is supplemented with an organic solvent that forms azeotrope with water, until water is finally replaced with the organic solvent, whereby the optically active amino acid amide is obtained in the organic solvent phase and the optically active amino acid is obtained as crystals.

The optically active amino acid precipitated as crystals is collected by a known method such as centrifugation or filtration. As a result, the optically active amino acid amide dissolved in the solution and the crystalline optically active amino acid can be separated from each other.

Further, an embodiment of the present invention will be described in detail as follows. That is, cells of microorganisms or treated products thereof having an activity to specifically hydrolyze the amide bond of D-2-amino-n-butyric acid amide are added to an aqueous solution containing D,L-2-amino-n-butyric acid amide hydrochloride so as to perform the reaction. Next, the cells or treated products thereof are removed from the reaction suspension by centrifugation or the like. The aqueous solution containing unreacted L-2-amino-n-butyric acid amide and reacted D-2-amino-n-butyric acid together with at least one member selected from the group consisting of an acid, a base, and a salt, is neutralized with an acid or a base, and then desalted by an electrodialysis process as it is or after made basic by addition of ammonia. After the desalted aqueous solution is concentrated, 2-methyl-1-propanol is added to the solution, and the precipitated insoluble crystals are separated by filtration. Thereby, crystals of D-2-amino-n-butyric acid are collected separately from L-2-amino-n-butyric acid amide remaining in the filtrate.

EXAMPLES

Next, the present invention will be specifically explained by way of working examples and comparative examples. The present invention is not, however, restricted to these examples.

Example 1

According to the method described in Japanese Patent Laid-Open No. 2002-253294, *Ochrobactrum anthropi* ATCC49237 was cultured. Then, the culture was centrifuged to prepare a cell suspension. After 353 g of D,L-2-amino-n-butyric acid amide hydrochloride was dissolved in 1000 g of water, the pH of the solution was adjusted to 7 with a 20% (by weight) NaOH aqueous solution, and water was added to the solution till it weighed 2000 g in total. The above-mentioned cell suspension was added to the D,L-2-amino-n-butyric acid amide aqueous solution so that the solution contained the cells in an amount of 2.6 g on dry weight basis, and the reaction was performed at 40° C. for 22 hours. After the reaction, the reacted solution was subjected to centrifugation to remove the cells, and was analyzed by HPLC and ion concentration analyzer. As a result, concentrations of L-2-amino-n-butyric acid amide and D-2-amino-n-butyric acid were both 6.3% by weight, and the thus-produced D-2-amino-n-butyric acid was almost optically pure (D isomer). Further, the solution contained Na ion at a concentration of 2.5% and Cl ion at a concentration of 7.7%, and showed weak acidity. After 1200 g of the enzymatically-reacted aqueous solution containing L-2-amino-n-butyric acid amide and D-2-amino-n-butyric acid was made ammoniacally basic by addition of 245 g of 25% ammonia water, the aqueous solution was desalted by electrodialysis. The electrodialysis was performed using an apparatus MICRO ACILYZER S3 (Asahi Kasei Corp.) equipped with ion exchange membranes K192D and A201F. The electrodialysis was performed at an applied voltage of 10.0 V, using a 1% sodium chloride aqueous solution as a dialyzate solution into which the salt moves and a 5% ammonium sulfate aqueous solution as an electrode solution. When the conductivity converged on nearly 15 to 20 mS, the electrodialysis was terminated. The aqueous solution after desalting weighed 1016 g, and contained L-2-amino-n-butyric acid amide and D-2-amino-n-butyric acid both of which had a concentration of 7% by weight. Yields of L-2-amino-n-butyric acid amide and D-2-amino-n-butyric acid were both 94%. After 20 g of the desalted solution was concentrated at 40° C. under reduced pressure and dried at 40° C. in vacuum, 20 g of 2-methyl-1-propanol was added to the resultant mixture, followed by stirring at room temperature for 2 hours. Then, insoluble crystals were separated by filtration under reduced pressure. The insoluble crystals weighed 1.36 g, and were composed of 99% by weight (1.35 g) of D-2-amino-n-butyric acid and 1% by weight (0.01 g) of L-2-amino-n-butyric acid amide. Yield of D-2-amino-n-butyric acid after the enzymatic reaction was 94%. On the other hand, the filtrate weighed 19.8 g, and contained L-2-amino-n-butyric acid amide at a concentration of 7% by weight (1.39 g) and D-2-amino-n-butyric acid at a concentration of 0.3% by weight (0.06 g). Yield of L-2-amino-n-butyric acid amide after the enzymatic reaction was 94%.

Example 2

The experiment was performed in the same manner as in Example 1 except that the aqueous solution was made neutral with addition of 82 g of 25% ammonia water. As a result, the insoluble crystals weighed 1.30 g, and were composed of 99% by weight (1.29 g) of D-2-amino-n-butyric acid and 1% by weight (0.01 g) of L-2-amino-n-butyric acid amide. Yield of D-2-amino-n-butyric acid after the enzymatic reaction was 94%. On the other hand, the filtrate weighed 19.0 g, and contained L-2-amino-n-butyric acid amide at a concentration of 7% by weight (1.33 g) and D-2-amino-n-butyric acid at a concentration of 0.3% by weight (0.06 g). Yield of L-2-amino-n-butyric acid amide after the enzymatic reaction was 90%.

Comparative Example 1

The aqueous solution containing L-2-amino-n-butyric acid amide and D-2-amino-n-butyric acid (300 g) which was obtained by the enzymatic reaction in Example 1, was desalted by electrodialysis as it was. After desalting, the aqueous solution weighed 155 g, and contained L-2-amino-n-butyric acid amide at a concentration of 0.15 wt % with 1.2% (0.23 g) yield, and contained D-2-amino-n-butyric acid at a concentration of 8.45 wt % with 69% (13.1 g) yield; thus a great loss resulted.

Comparative Example 2

The aqueous solution containing L-2-amino-n-butyric acid amide and D-2-amino-n-butyric acid (20 g) which was obtained by the enzymatic reaction in Example 1, was concentrated at 40° C. under reduced pressure as it was. After 20 g of 2-methyl-1-propanol was added to the concentrated solution, the mixture was stirred at room temperature for 2 hours, and then insoluble crystals were separated through filtration under reduced pressure. The insoluble crystals weighed 1.96 g, and were composed of 57.5% by weight (1.13 g) of D-2-amino-n-butyric acid and 42.5% by weight (0.833 g) of L-2-amino-n-butyric acid amide. On the other hand, the filtrate weighed 19.6 g, and contained L-2-amino-n-butyric acid amide at a concentration of 2.9% by weight (0.57 g) and D-2-amino-n-butyric acid at a concentration of 1.4% by weight (0.27 g). Thus, it was impossible to separate L-2-amino-n-butyric acid amide and D-2-amino-n-butyric acid from each other.

INDUSTRIAL APPLICABILITY

According to the present invention, efficient separation and collection of an optically active amino acid amide or an optically active amino acid which is an important intermediate in the production of various industrial chemicals, agricultural chemicals and pharmaceuticals are made possible by use of organic solvents, and thus the invention is useful in the fields of various industrial chemicals, agricultural chemicals, and pharmaceuticals.

The invention claimed is:

1. A method for separately collecting an optically active amino acid amide and an optically active amino acid from an aqueous solution containing the optically active amino acid amide and the optically active amino acid together with at least one member selected from the group consisting of an acid, a base and a salt, which comprises:

a neutralization step of neutralizing an acid or a base when said aqueous solution contains the acid or the base, a desalting step of removing the salt contained in said aqueous solution and/or formed in said neutralization step, and a step of collecting the optically active amino acid amide and the optically active amino acid separately from each other from said aqueous solution which has been desalted in said desalting step, by a process which takes advantage of a difference in solubility between said two components in an organic solvent.

2. The method according to claim 1, wherein said desalting step is performed with ammonia added to said aqueous solution.

3. The method according to claim 2, wherein ammonia is added in an amount of 0.01 to 100 times by mole the optically active amino acid amide.

4. The method according to claim 1, wherein said desalting step is performed by an electrodialysis process.

5. The method according to claim 1, wherein the optically active amino acid amide is L-2-amino-n-butyric acid amide.

6. The method according to claim 1, wherein the optically active amino acid is D-2-amino-n-butyric acid.

7. The method according to claim 2, wherein said desalting step is performed by an electrodialysis process.

* * * * *